United States Patent [19]

Cheng et al.

[11] Patent Number: 5,120,876

[45] Date of Patent: Jun. 9, 1992

[54] FLUORINATED SULFONES/KETONES FOR NONLINEAR OPTICS

[75] Inventors: Lap T. Cheng, Newark; Andrew E. Feiring, Wilmington, both of Del.; Wilson Tam, Boothwyn, Pa.

[73] Assignee: E. I. Du Pont de Nemours and Company, Wilmington, Del.

[21] Appl. No.: 486,672

[22] Filed: Feb. 28, 1990

Related U.S. Application Data

[63] Continuation of Ser. No. 442,677, Nov. 29, 1989, abandoned.

[51] Int. Cl.$^5$ ............................................. C07C 381/12
[52] U.S. Cl. ...................... 564/440; 564/305; 564/307; 568/39; 568/58; 568/635; 568/308; 568/325; 568/331; 568/335; 548/565; 548/569; 544/358; 544/392
[58] Field of Search ............... 564/307, 305, 440; 558/56, 58, 55; 568/39, 58, 635

[56] References Cited

U.S. PATENT DOCUMENTS

| | | | |
|---|---|---|---|
| 3,895,062 | 7/1975 | Harrington et al. | 260/556 F |
| 4,551,264 | 11/1980 | Eidenschink et al. | 564/307 X |
| 4,792,208 | 12/1988 | Ulman et al. | 350/96.34 |
| 4,818,898 | 4/1989 | Anderson et al. | 307/427 |
| 4,837,327 | 6/1989 | Stahly | 546/24 |

OTHER PUBLICATIONS

Franken et al., Physical Review Letters, 7, 118-119 (1961).
Material for Nonlinear Optics Chemical Perspectives, Seth R. Marder et al. Eds., Americal Chemical Society, 1990.
Nonlinear Optical Properties of Organic Molecules and Crystal, D. S. Chemla and J. Zyss, Ed., vol. 1, Academic Press, Inc. (1987), 227-235.

*Primary Examiner*—Glennon H. Hollrah
*Assistant Examiner*—Shailendra Kumar

[57] ABSTRACT

This invention relates to optical elements capable of second harmonic generation and novel compositions for use in such optical elements comprising polar molecules placed in noncentrosymmetric configuration wherein such optical element has an electron donor moiety linked through a conjugated bonding moiety to an electron acceptor moiety which consists of a selected fluorinated sulfone, fluorinated ketone, fluorinated vinyl sulfone or fluorinated alkyl vinyl sulfone.

4 Claims, 2 Drawing Sheets

FLUORINATED SULFONES/KETONES FOR NONLINEAR OPTICS

This application is a continuation of Ser. No. 07/442,677 filed Nov. 29, 1989, now abandoned.

FIELD OF THE INVENTION

This invention relates to optical elements, and compositions for use in such optical elements, which exhibit effects attributable to the nonlinear optical properties of the element. More specifically, the invention relates to optical elements containing a transmission medium comprising polar aligned noncentrosymmetric molecular dipoles having an electron donor moiety linked through a conjugated bonding moiety to an electron acceptor moiety which is a selected fluorinated sulfone, fluorinated ketone, or a fluorinated vinyl sulfone, fluorinated alkyl vinyl sulfone or fluorinated sulfonylsulfimide. The optical elements described herein are particularly useful in optical devices requiring second harmonic generation (hereinafter SHG). Second harmonic generation may be used, for example, to vary the frequency of a diode laser, for information control in optical circuitry, and optical switches.

BACKGROUND OF THE INVENTION

It has been recognized that certain media having a polarization susceptability provide sensitive ways of manipulating beams of incident electromagnetic radiation. Such media are said to possess nonlinear polarization. The size of the effects attributable to such nonlinear polarization depends on the arrangement of electrically charged particles (electrons, ions and nuclei) within the media. To obtain the highest nonlinear polarizaton property of a medium, the molecules within the medium must be arranged so that the nonlinear properties of the individual polar molecules within the medium do not cancel each other out.

On a molecular level the polarization of a medium can be described by the following expression:

$$\mu = \mu_0 + \alpha E + \beta EE + \gamma EEE + \ldots$$

where $\mu$ is the induced dipole moment
$\mu_0$ is the permanent dipole moment
E is local electric field
$\alpha$, $\beta$, and $\gamma$ are tensors representing the linear, second order and third order polarizabilities, respectively. $\beta$ and $\gamma$ are also referred to as the first and second hyperpolarizabilities, respectively.

On the molecular level first order or linear polarization is described by $\alpha E$; second order or first nonlinear polarization by $\beta EE$; and third order or second nonlinear polarization by $\gamma EEE$.

The polarization of an ensemble of molecules induced by an applied electric field can be described by the following expression:

$$P = P_0 + \chi^{(1)}E + \chi^{(2)}EE + \chi^{(3)}EEE + \ldots$$

where
P is the induced polarization
$P_0$ is the permanent polarization
E is the applied electric field
$\chi^{(1)}$, $\chi^{(2)}$ and $\chi^{(3)}$ are tensors representing the linear, second order and third order polarization susceptibilities, respectively.

$\chi^{(2)}$ arises from the second order molecular polarizability or first hyperpolarizability, $\beta$, and $\chi^{(3)}$ arises from further hyperpolarizabilities, etc. As tensor quantities, the susceptibilities, $\chi^{(i)}$, are highly symmetry dependent; odd order coefficients are nonvanishing for all materials, but even order coefficients, e.g., $\chi^{(2)}$, are nonvanishing only for noncentrosymmetric materials.

Franken et al., Physical Review Letters, 7, 118–119 (1961), disclose the observation of second harmonic generation (SHG) upon the projection of a pulsed ruby laser beam through crystalline quartz. The use of a laser remains the only practical way to generate an E large enough to be able to detect the SHG phenomenon.

Second order nonlinear optical phenomena, such as SHG, sum and difference frequency generation, parametric processes and electro-optical effects, all arise from the $\chi^{(2)}$ term. Consequently, for significant nonlinear optical phenomena it is desirable that a molecule possess a large hyperpolarizability, $\beta$, and that an ensemble of such molecules possess a large $\chi^{(2)}$.

The art has recognized that organic molecules having conjugated $\pi$-electron systems or low-lying charge transfer excited states often have extremely large hyperpolarizabilities, but unfavorable alignment of the molecules in the crystalline phase, in thin films or in other forms can result in a centrosymmetric material in which the $\chi^{(2)}$ vanishes. This problem may be circumvented by using a chiral molecule to insure a noncentrosymmetric (i.e., symmetrical about its center) crystal, but problems associated with the creation and maintenance of a high level of optical purity limit the value of this approach. In addition, optical activity per se does not guarantee that $\chi^{(2)}$ will be large, only that it will not be zero.

One approach to the problem disclosed by Anderson et al. U.S. Pat. No. 4,818,898 involves the formation of inclusion complexes consisting of a crystalline lattice forming host compound with continuous channels containing a nonlinearly polarizable guest compound having a second order polarizability greater than $10^{-30}$ electrostatic units.

Ulman et al. U.S. Pat. No. 4,792,208 discloses an optical article containing a medium exhibiting a second order polarization susceptibility greater than $10^{-9}$ electrostatic units comprised of polar aligned noncentrosymmetric molecular dipoles having an electron donor moiety linked through a conjugated $\pi$ bonding system to an electron acceptor moiety to permit oscillation of the molecular dipole between a lower polarity ground state and a higher polarity excited state. A wide variety of donor and acceptor moieties are disclosed with a sulfonyl electron acceptor group in combination with a hydrocarbon substituted electron donor group preferred. The second order nonlinearity is achieved by the polar alignment of the molecular dipoles, in, for example, polymeric binders, to form Langmuir-Blodgett (LB) films.

While the art continues to investigate the alteration of chemical structure to continuously increase molecular nonlinearity and corresponding molecular dipole moment, this approach may not always produce the material having the best combination of overall properties. Large dipole moment, which favors strong polar alignment, can often be associated with aggregation and solubility problems, allowing only a small amount of optically active material to be contained in a binder.

Furthermore alterations in chemical structure to increase nonlinearity can often adversely effect the color of the resulting material. Since the first and second harmonic wavelengths of diode lasers lie near 800 and 400 nanometers, respectively, the optimum nonlinear molecules must have high transparency, i.e., very low absorption at these wavelengths, and, in addition, possess high photochemical stability under the conditions of exposure to high optical intensities. One of the major chemical challenges in this area of technology is to discover molecules that have high nonlinearity, but absorb very little light over the visible range of wavelengths from 350 to 850 nanometers.

Accordingly, it is an object of this invention to provide a novel nonlinear optical medium which exhibits a high transparency over the visible range of wavelengths.

It is another object of this invention to provide a nonlinear optical element comprising a transparent medium selected from fluorinated sulfones and fluorinated ketones.

It is a further object of this invention to provide a novel composition which is a physical blend of fluorinated sulfones or ketones with a polymer component.

It is an additional object to provide an apparatus for second harmonic generation.

These and other objects and advantages will become apparent from the accompanying description and examples.

SUMMARY OF THE INVENTION

The present invention provides for compounds exhibiting high nonlinearity and high transparency namely little or no absorption at 390 nm→850 nm wavelength selected from fluorinated sulfones and fluorinated ketones of the following formulas:

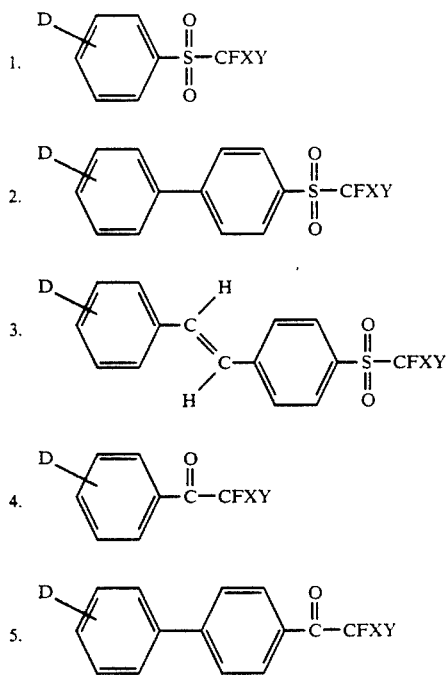

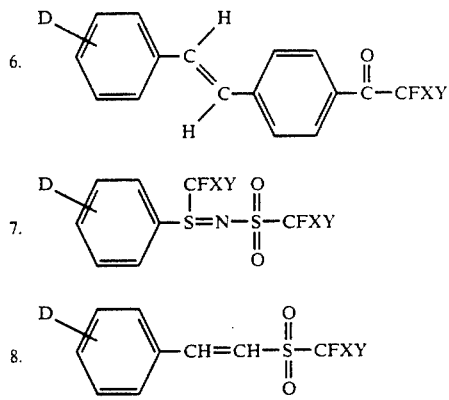

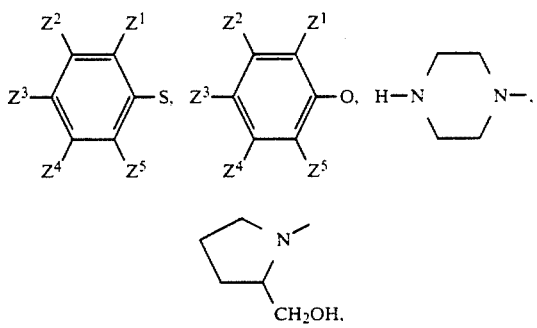

wherein
D is an electron donor moiety selected from $NH_2$, $NHR^1$, $N(C_nH_{2n+1})_2$, $N(C_nH_{2n+1})(C_nH_{2n}OH)$, $N(C_nH_{2n}OH)_2$, $N(C_nH_{2n+1})N(C_nH_{2n+1})_2$, $N=C(C_nH_{2n+1})_2$, $OC_nH_{2n+1}$, $SC_nH_{2n+1}$, branched or straight chain alkyls having from 2 to 20 carbons, F, and Br,
wherein n=0 to 20
$Z^1$, $Z^2$, $Z^3$, $Z^4$ and $Z^5$ are individually selected from H, alkyl of 1 to 20 carbon atoms, aryl, $OR^2$, $SR^3$ and $NR^4R^5$,
$R^1$, $R^2$, $R^3$, $R^4$ and $R^5$ are individually selected from aryl, alkyl of from 1 to 20 carbon atoms, and $COR^6$, wherein $R^6$ is selected from H, aryl, and alkyl of from 1 to 20 carbon atoms,
X and Y are the same or different and are individually selected from H, F, Cl, Br, I, alkyl and fluoroalkyl of 1 to 20 carbon atoms, aryl, fluoroaryl, SR and $OR^7$, wherein $R^7$ is selected from alkyl of 1 to 20 carbon atoms and aryl,
with the following provisos (1) for structures 1 and 4 that when D is $NH_2$, F, Br, $NH(C_2H_5)$, $N(CH_3)_2$, $OCH_3$, OH or SH, X is not F and Y is not a fluoroalkyl of less than 7 carbon atoms; (2) for structure 7 that when D is H, p-Cl, p-F, m-F, p-$NO_2$ or p-$NH_2$ and X and Y are not F; and (3) for structure 8 that when D is $OC_nH(2n+1)$, n is not 1.

It is preferred that X is F and Y is fluoroalkyl of 1 to 20 carbon atoms. It is more preferred that X is F and Y is a perfluoroalkyl of 2 to 10 carbon atoms.

Metal complexation is also effective in conjunction with the selection of D in the above formulas. When metal complexation is employed, D is selected from substituents of the formula $M(L)_2X'$, wherein M is selected from Pt and Pd, and wherein L is selected from triaryl phosphine and trialkyl phosphine of from 1 to 20 carbon atoms and wherein X' is selected from F, Cl, Br, I, —SCN, —NCO, —NO$_2$, —CN, and SnCl$_3$.

The invention also provides for an improved optical element containing a transmission medium comprising polar aligned molecular dipoles, arranged in non-centrosymmetric configuration, having an electron donor moiety linked through a conjugated $\pi$ bonding system to an electron acceptor moiety. The improvement resides in the electron acceptor moiety being selected from SO$_2$CFXY, CH=CHSO$_2$CFXY, COCFXY and CFXYS=NSO$_2$CFXY, wherein X and Y are the same or different and are individually selected from H, F, Cl, Br, I, alkyl and fluoroalkyl of 1 to 20 carbon atoms, aryl, fluoroaryl, SR$^7$ and OR$^7$, wherein R$^7$ is selected from alkyl of 1 to 20 carbon atoms and aryl. It is preferred that X=F or perfluoroalkyl of 1 to 20 carbon atoms and that Y=perfluoroalkyl. It is most preferred that X=F and Y=perfluoroalkyl of 2 to 10 carbon atoms.

The optical element may be employed in various forms including as a solution or dispersion in a polymer which is then subjected to an electrical field to align the polar molecules or as a film (e.g., Langmir-Blodgett (LB) film) or possibly as a macroscopic crystal of the compound selected or as a solution of the compound which is then subjected to an electrical field to align the polar molecules.

DETAILED DESCRIPTION OF THE INVENTION

In accordance with this invention it has been found that utilizing an electron acceptor moiety of the sulfonyl or carbonyl type wherein the carbon adjacent to the sulfonyl or carbonyl group has at least one fluorine substituent provides a molecule possessing enhanced dipole moment, and correspondingly high nonlinearity, without a significant sacrifice in transparency. As the degree of further fluorine substitution on the alkyl chain increases, the dipole moment and corresponding nonlinearity tends to increase. For both electron acceptor moieties of the sulfonyl type and the carbonyl type the observed effect, i.e., nonlinearity enhancement over unfluorinated sulfone and ketones, is largest for the molecules in which the conjugated $\pi$ bonding system is benzene, somewhat less for biphenyl, and least for stilbenes. The magnitude of the effect is greater for the electron acceptor moieties of the sulfonyl type than for those of the carbonyl type. Utilizing the fluorinated sulfonylsulfimide group as shown in structure 7 results in larger dipole moment and comparable $\beta$ relative to comparable fluorinated sulfone group. For example, 4-methoxy-4'-perfluorohexylsulfonylbiphenyl has a $\mu$ of 5.9 and $\beta$ of $9.1 \times 10^{-30}$ esu ($\mu\beta = 54$ units) while the analogous compound with the fluorinated sulfonylsulfimide group, 4-methoxy-4'-S-perfluoropropyl-N-trifluoromethylsulfonylsulfimide biphenyl, has $\mu$ of 7.9 and $\beta$ of $9.4 \times 10^{-30}$ esu ($\mu\beta = 74$ units). Due to the larger dipole moment, the use of the fluorinated sulfonylsulfimide group offers advantages in poled polymer applications.

To determine the molecular hyperpolarizability, $\beta$, for the compounds useful in the practice of the invention a set of physical and optical measurements were carried out in accordance with procedures in the art. These include, on a series of solutions with graded concentrations, measurements of density, refractive index at several wavelengths, capacitance, THG, and EFISH amplitudes and coherence lengths. These measurements respectively determine the specific volume of a solute molecule in solution, solution dispersion, solution dielectric properties, and the THG and EFISH nonlinear susceptibilities for each solution. All measurements, except THG and EFISH measurements which are described herein below with reference to FIG. 1, were performed according to well established procedures in the art. With the measured solution properties, following the full Onsager local field model (C. J. F. Bottcher, "Theory of Electrical Polarization", 2nd ed. Elsevier, N.Y., 1973) and taking the infinite dilution limit (K. D. Singer and A. F. Garito, J. Chem Phys. 75 (1981) 3572-3580), the relevant molecular properties including the dipole moment, $\mu$, the low frequency linear polarizability, $\alpha$, the molecular hyperpolarizability, $\beta$, and the second molecular hyperpolarizability, $\gamma$, were calculated.

Figure 1:
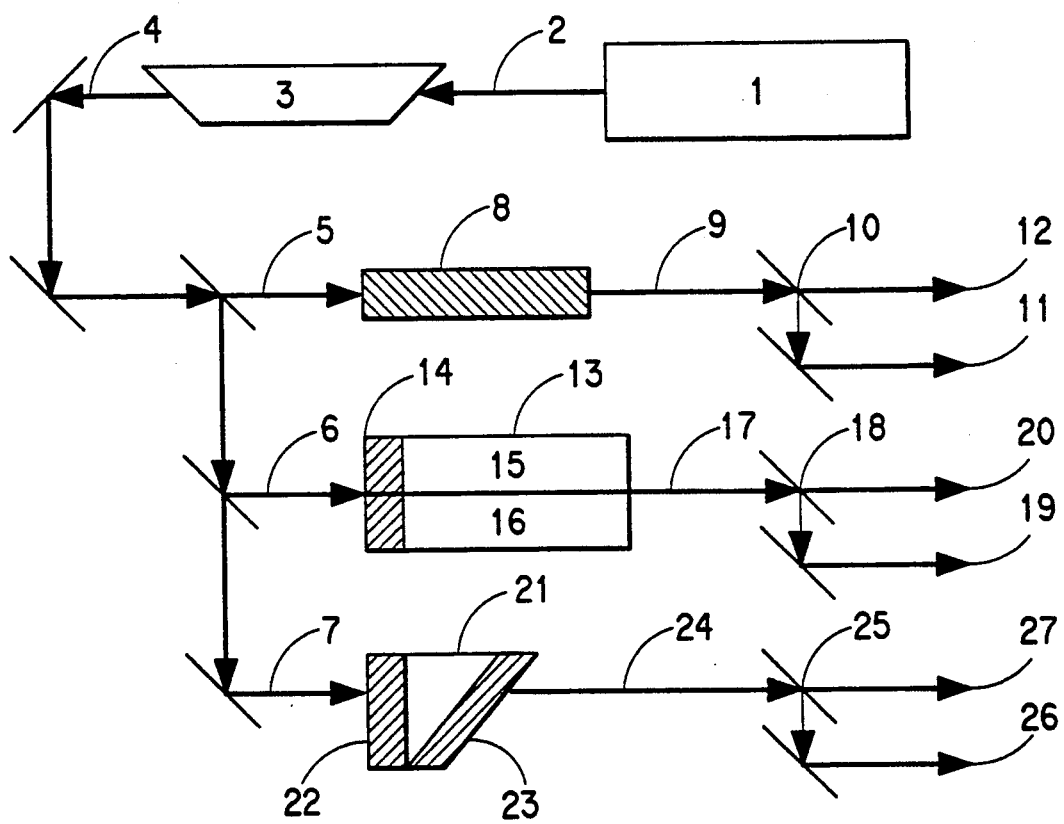
FIG. 1 is a schematic view of the apparatus for determining the field induced second harmonic generation (EFISH) and the third harmonic generation (THG).

FIG. 1 is a schematic view of the optical setup used for EFISH and THG measurements. A 20 Hz Nd:YAG laser 1 provides 10 ns pulses of 0.4 J energy. The 1.06 $\mu$m output 2 pumps a hydrogen Raman shifter 3 which provides up to 120 mW of Stokes radiation 4 at a frequency of 1.91 $\mu$m. The Stokes radiation 4 serves as the fundamental frequency for both the EFISH and THG measurements with harmonic wavelengths at 954 nm and 636 nm, respectively. The Stokes radiation is divided into three ways into beams 5, 6, and 7, respectively. Beam 5 is passed through reference channel 8 constructed of a nonlinear crystalline material, such as quartz. The resulting beam 9 is separated by dichroic mirrors 10 (a single dichroic mirror is at each optical branch) into second and third harmonic signals, 11 and 12, to determine normalization intensity. Beam 6 is passed through an amplitude cell 13. Amplitude cell 13 contains a 2 cm thick front window 14 through, which beam 6 passes, and is divided into sections 15, containing a liquid of known optical properties, e.g., toluene, and 16, containing a solution of a compound useful in the practice of this invention in an appropriate solvent such as p-dioxane or chloroform. Gold electrodes are fabricated at the window-liquid interface so that both EFISH and THG measurements can be carried out concurrently, in accordance with the procedure described in L.- T. Cheng et al., SPIE Vol. 1147 (1989). The resulting beam 17 is separated by dichroic mirrors 18 into second and third harmonic signals, 19 and 20, for measurement of harmonic amplitude. Beam 7 is directed through a wedge shaped cell 21 having quartz windows 22 and 23 and containing an equivalent solution of a compound useful in the practice of this invention as contained in section 16, for measurement of the coherence lengths. The resulting beam 23 is separated by dichroic mirrors 25 into second and third harmonic signals, 26 and 27.

The optical element in accordance with the invention may in some cases consist of a macroscopic crystal of the compound chosen, providing the compound can be made to form crystals in which the polar molecules are in noncentrosymmetric alignment. Such crystals may be grown at a slow rate under equilibrium with their mother liquor by a variety of methods practiced in the art. However, this procedure will not work for many polar molecules due in large part to dipole interactions. Another method of producing a useful optical element involves dissolving the compound in a solvent, which can be placed in a container having the desired shape. The solution can then be subjected to an electrical field which causes the dissolved dipoles to align themselves in the field. Electromagnetic radiation can then be passed through the solution and nonlinear optical effects, such as second harmonic generation, can be produced. Both the presence of an electric field and the need to utilize the compound in liquid solution form may be inconvenient or undesirable in some applications.

A particularly convenient and effective form of the optical element in accordance with the invention involves dispersing the polar molecules in a polymeric binder. The polar molecules can be mixed into the polymeric binder or grafted onto the polymer. The mixture can be heated to a temperature at which the polymer becomes sufficiently soft so that upon application of an electrical field the polar molecules line up in the direction of the field. When the mixture cools, the polar molecules are locked into their aligned positions, after which the electric field can be removed. Suitable binders include polymethacrylate, poly(methyl methacrylate), poly(vinyl alcohol), copolymers of methyl methacrylate and methacrylic acid, copolymers of styrene and maleic anhydride and half ester-acids of the latter, as well as many others. It is highly preferred that the polymeric binder of choice be highly transparent so that the transparency of the compounds utilized in the practice of this invention can be advantageously employed.

One common form the optical element can take is that of a Langmuir-Blodgett (LB) film. A small amount of a compound useful in the practice of this invention spread on the surface of a liquid forms a surface film of monomolecular thickness at the air/liquid interface. If the supporting liquid is a polar liquid, such as water, the hydrophilic moieties of the compound are drawn into the liquid, while the hydrophobic moieties of the compound are attracted to the non-polar, air side of the interface to hold the polar molecules at the surface of the supporting liquid body, resulting in polar alignment of the polar molecules on the surface of the supporting liquid. When the supporting substrate is slowly immersed in the film bearing liquid body or slowly withdrawn from it, an oriented monomolecular film is formed on the substrate.

Figure 2:
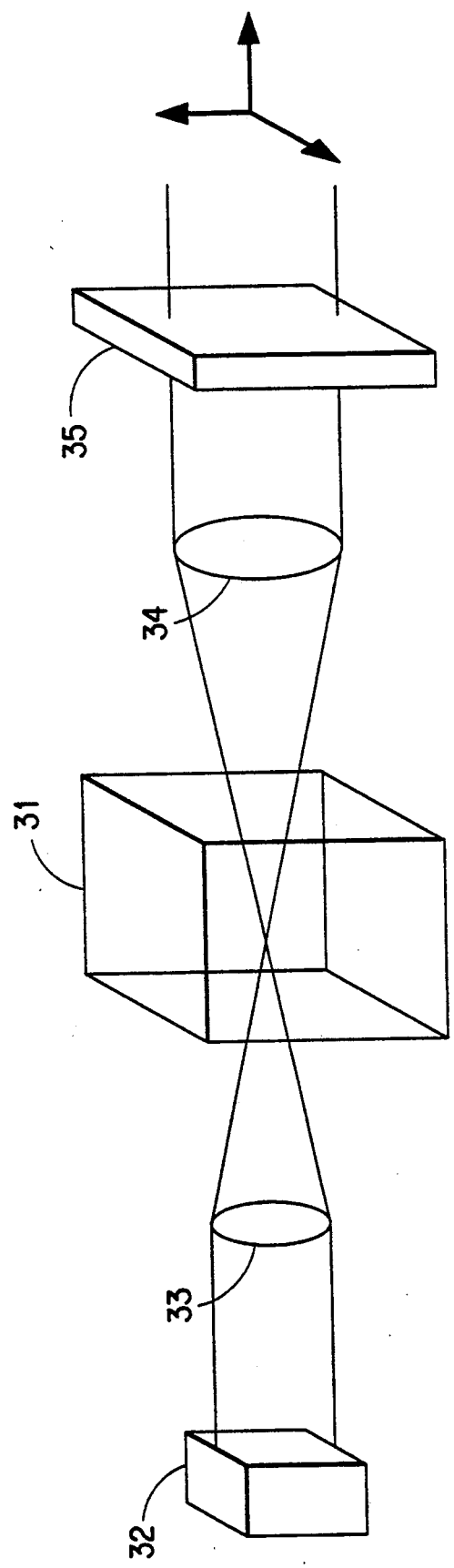
FIG. 2 is a schematic view of a nonlinear optical device according to the invention.

The nonlinear optical device according to the invention comprises a means to direct at least one incident beam of electromagnetic radiation onto an optical element having nonlinear optical properties whereby electromagnetic radiation emerging from the element contains at least one frequency different from the frequency of any incident beam of radiation, the different frequency being an even multiple of the frequency of one incident beam of electromagnetic radiation. The optical element is selected from one of the forms described above. Preferably, the emerging radiation of a different frequency is doubled, i.e. SHG. Referring now to FIG. 2, optical element 31 is oriented to achieve at least partially maximized SHG by virtue of phase matching, the specific orientation chosen for reasons of noncriticality, maximum nonlinearity, increased angular acceptance, etc. Polarized light, for example, of wavelength 1.06 μ from a Nd YAG laser 32, is incident on the optical element along the optical path. A lens 33 focuses the light into the optical element. Light emerging from optical element 31 is collimated by a similar lens 34 and passed through a filter 35 adapted to remove light of the initial wavelength, e.g., 1.06 μ, while passing light of ½ the wavelength of the incident light, e.g., 0.53 μ.

The optical element of the invention can also utilized in an electro-optic modulator, wherein an electric field is applied to the optical element in a direction to modify the transmission properties of the element.

EXAMPLES

The following illustrate specific embodiments of the invention. SHG was measured by the powder method of Kurtz et al., J. Appl. Phys., Vol. 39, 3798 (1968), using a Nd YAG laser (wavelength 1,064 μm) and urea as a reference. The polycrystalline urea powder used as a reference had an average particle size of 90 μm to 125 μm. The intensity of the second harmonic radiation generated by the sample was thus measured relative to that provided by urea.

Compounds 1–5 were prepared by adapting literature procedures. The sodium salt of 4-fluorobenzenethiol was reacted (see V. N. Boiko, G. M. Shchupak and L. M. Yagupolskii, J. Org. Chem. USSR (Engl. Trans.) 1977, 13, 972; V. I. Popov, V. N. Boiko and L. M. Yagupolskii, J. Fluorine Chem. 1982, 21, 365; A. E. Feiring, J. Fluorine Chem. 1984, 24, 191; V. I. Popov, V. N. Boiko, N. V. Kondratenko, V. P. Sampur and L. M. Yagupolskii, J. Org. Chem. USSR (Engl. Trans.) 1977, 13, 1985; V. N. Boiko, T. A. Dashevskaya, G. M. Shchupak and L. M. Yagupolskii, J. Org. Chem. USSR (Engl. Trans.) 1979, 15, 347) with perfluorodecyl iodide to give an intermediate phenyl perfluoroalkyl sulfide (not shown) which was oxidized to the sulfone 1 using chromium trioxide (see, N. V. Kondratenko, V. I. Popov, A. A. Kolomeitsev, E. P. Saenko, V. V. Prezhdo, A. E. Lutskii and L. M. Yagupolskii, J. Org. Chem. USSR (Engl. Trans.) 1980, 16, 1049). The products illustrated by 2–5 below were prepared by reaction of compound 1 with nucleophiles HY. See V. I. Popov, A. A. Kolomeitsev and T. I. Cherepenko, Fiziol. Akt. Verhchestra 1980, 12, 36 (Chem. Abstr. 95:425462). Specific procedures are given in the examples below.

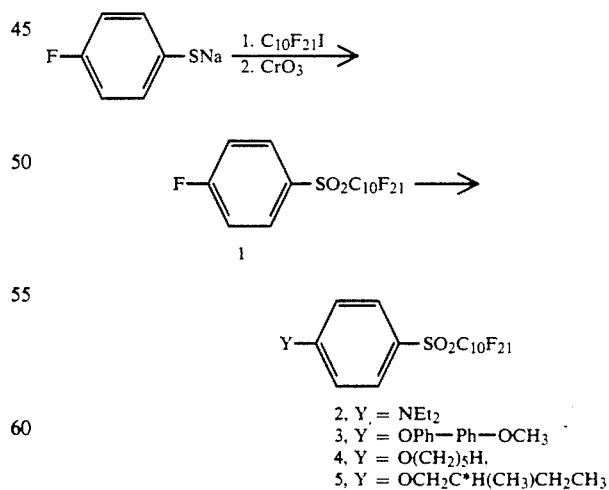

2, Y = NEt₂
3, Y = OPh—Ph—OCH₃
4, Y = O(CH₂)₅H.
5, Y = OCH₂C*H(CH₃)CH₂CH₃

Compounds 6, 7 and 8 of Table 1 were prepared by the process described in X. Creary, J. Org. Chem. 52, (1987) 5026. A reference for cross coupling chemistry (compounds 3 and 6) is B. A. Patel, C. B. Ziegler, N. A. Cortese, J. E. Plevyak, T. C. Zebovitz, M. Terpko and R. F. Heck, J. Org. Chem., Vol. 42, No. 24, 1977, 3903. References for preparing biphenyl using borinic acids (as in compounds 2 and 5) are 1) N. Migaura, T. Yanagi, and A. Suzuki, Synthetic Communications, 11(7) (1981) 513, and 2) W. J. Thompson and J. Gaudino, J. Org. Chem., 49 (1984) 5240.

The vinyl sulfones were prepared using a literature procedure: R. Sodoyer, E. Abad, E. Rouvier, and A. Cambon, Journal of Fluorine Chemistry, 22 (1983) 401–419. $CH_3SO_2(CF_2)_2C(OMe)(OCH_2CF_3)(CF_3)$ was used as a starting material. It may be produced from the process described by C. G. Krespan and B. E. Smart, J. Org. Chem. (1986), 51, 320. Vinyl sulfones of the type aryl-CHCH-$SO_2Rf$ were prepared where Rf is $(CF_2)_2C(OMe)(OCH_2CF_3)(CF_3)$.

Condensation of 3-methyl-p-anisaldehyde with $CH_3SO_2(CF_2)_2C(OMe)(OCH_2CF_3)(CF_3)$.

To 0.50 g (1.28 mmoles) of $CH_3SO_2(CF_2)_2C(OMe)(OCH_2CF_3)(CF_3)$ and 0.202 g (1.35 mmoles) of 3-methyl-p-anisaldehyde in 10 mL of ethanol at 0° C. was added a catalytic amount of NaOEt in 5 mL of EtOH (prepared by dissolving a sphere of Na in 5 mL of ethanol). The mixture was warmed to room temperature and stirred overnight. The solvent was removed by rotary evaporation and the residue was chromatographed on silica gel eluted with $CH_2Cl_2$. Thus obtained was 0.471 g (0.90 mmoles, 70%) of product as a light yellow solid.

Elemental analysis: calculated for $C_{17}H_{16}O_5F_{10}S$: C: 39.09; H: 3.09; Found: C: 38.81; H: 3.33.

$^1H$ NMR ($CD_2Cl_2$): 7.73 (d, J=15.3 Hz, 1H), 7.45 (m, 3H), 6.91 (d, J=8 Hz, 1H), 6.66 (d, J=15.3 Hz, 1H), 4.18 (q, J=8 Hz, 2H), 3.89 (s, 3H), 3.67 (s, 3H). SHG: 0.006×urea. EFISH data: $\lambda_{max}$: 316 nm, $\mu = 5.5 \times 10^{-18}$ esu; $\beta = 14 \times 10^{-30}$ esu.

Condensation of 4-N,N-dimethylaminobenzaldehyde with $CH_3SO_2(CF_2)_2C(OMe)(OCH_2CF_3)(CF_3)$.

Use the same procedure as above but with 1.00 g (2.56 mmoles) of $CH_3SO_2(CF_2)_2C(OMe)(OCH_2CF_3)(CF_3)$ and 0.282 g (2.56 mmoles) of 4-N,N-dimethylaminobenzaldehyde. After chromatography on silica gel eluted with $CHCl_3$ was obtained 0.970 g (1.86 mmoles, 73%) of the desired product as a yellow solid. Elemental analysis calculated for $C_{17}H_{17}NO_4F_{10}S$: C: 39.16; H: 3.29; found: C: 39.05; H: 3.09. $^1H$ NMR ($CD_2Cl_2$): 7.66 (d, J=15.1 Hz, 1H), 7.47 (d, J=8.9 Hz, 2H), 8.96 (d, J=6.89 Hz, 2H), 6.45 (d, J=15.1 Hz, 1H), 4.18 (q, J=8 Hz, 2H), 3.67 (s, 3H), 3.07 (s, 3H). SHG: 0.02×urea. EFISH data: $\lambda_{max}$: 376 nm, $\mu = 7.4 \times 10^{-18}$ esu; $\beta = 34 \times 10^{-30}$ esu.

The fluorinated sulfonylsulfimides have been prepared by reacting a fluorinated sulfoxide with a fluorinated sulfonylamine in a fluorinated sulfonic anhydride using a literature procedure: N. V. Kondratenko, V. I. Popov, G. N. Timofeeva, N. J. Ignat'ev, and L. M. Yagupol'skii, Zhurnal Organischeskoi Khimii, 20, 2367–2371, 1984. Specifically, compounds of formula 7, where D is H, p-Cl, p-F, m-F, p-$NO_2$ and p-$NH_2$ and X and Y are F were prepared by reacting the corresponding sulfoxide with $CF_3SO_2NH_2$ in trifluoromethanesulfonic anhydride. Embodiments of formula 7 in accordance with the invention were prepared by nucleophilic substitution from the known p-F derivative. The biphenyl derivative was prepared from Pd catalyzed cross coupling chemistry using the p-Br derivative and 4-methoxyphenylboronic acid using literature procedures: N. Migaura, T. Yanagi, and A. Suzuki, Synthetic Communications, 11, 513–519, 1981, and W. J. Thompson and J. Gaudino, J. Org. Chem., 49, 5237–5243, 1984.

The p-F-$C_6H_4S(C_3F_7)$=$NSO_2CF_3$ was prepared as follows: In 10 mL of $CH_2Cl_2$ was added 1.00 g (3.20 mmoles) of 4-fluorophenyl)perfluoropropyl sulfoxide, 0.477 g (3.20 mmoles) of trifluoromethanesulfonamide, and 0.904 g (3.20 mmoles) of trifluoromethanesulfonic anhydride. The mixture was stirred overnight and then added to ice. The mixture was extracted with $CH_2Cl_2$, dried over $MgSO_4$ and solvent removed. The solid was washed with hexane to remove starting material to give 0.348 g (0.78 mmoles, 24%) of the desired product. mp: 92°–96° C. Elemental analysis calculated for $C_{10}H_4NO_2F_{11}S_2$: C: 27.10, H: 0.91; Found: C: 27.14, H: 0.84 . $^1H$ NMR ($CD_2Cl_2$): 8.1 (m, 2H), 7.5 (m, 2H). $^{19}F$ NMR ($CD_2Cl_2$): −78.4 (s, 3F), −80.6 (t, J=9 Hz, 3F), −98.5 (m, 1F). −104.4 (d of q, J=221, 9 Hz, 1F), −110.2 (d of q, J=221, 8 Hz, 1F), −122.5 (s, 2F).

The p-F-$C_6H_4S(C_{10}F_{21})$=$NSO_2CF_3$ was prepared using the same procedure as above but with 662 mg (1.0 mmoles) of (4-fluorophenyl)perfluorodecyl sulfoxide, 564 mg (2.0 mmoles) of the anhydride and 298 mg (2.0 mmoles) of the trifluoromethanesulfonamide. Obtained 178 mg (0.22 mmoles, 22%) of the desired product. $^1H$ NMR ($CD_2Cl_2$): 8.0 (m, 2H), 7.5 (m, 2H). $^{19}F$ NMR ($CD_2Cl_2$): −78.4 (s, 3F), −81.0 (t, J=10 Hz, 3F), −98.4 (m, 1F), −103.0 (d of m, J=220 Hz, 1F), −109.0 (d of m, J=220 Hz, 1F), −118.0 (s, 2F), −121.8 (s, 10F), −122.5 (s, 2F), −126.3 (s, 2F).

The p-Br-$C_6H_4S(C_3F_7)$=$NSO_2CF_3$ was prepared using the same procedure as above but with 1.0 g (2.68 mmoles) of (4-bromophenyl)perfluoropropyl sulfoxide, 0.756 g (2.68 mmoles) of the anhydride and 0.400 g (2.68 mmoles) of trifluoromethanesulfonamide. Thus obtained was 393 mg (0.78 mmoles, 29%) of the desired product as an off-white solid. Elemental analysis calculated for $C_{10}H_{14}NO_2F_{10}S_2Br$: C: 23.82; H: 0.80; Found: C: 23.82, H: 0.70. $^{19}F$ NMR ($CD_2Cl_2$): −78.4 (s, 3F), −80.6 (t, J=9 Hz, 3F), −104.0 (d of q, J=220, 9 Hz, 1F), −109.9 (d of m, J=220 Hz, 1F), −122.4 (s, 2F).

The sulfoxides were prepared from the corresponding sulfide and m-chloroperoxybenzoic acid (MCPBA). A typical procedure follows for the preparation of (4-bromophenyl)perfluoropropyl sulfoxide:

MCPBA (4.330 g of 55%, 13.8 mmoles) was dissolved in 50 mL of $CH_2Cl_2$ and added to 75 mL of $CH_2Cl_2$ containing 4.93 g (13.8 mmoles) of (4-bromophenyl)perfluoropropyl sulfide at −78° C. The mixture was stirred at room temperature overnight. To the colorless solution was added 50 mL of 1M NaOH and the mixture extracted with 3×50 mL $CH_2Cl_2$, and dried over $MgSO_4$. The solvent was removed and the residue chromatographed on silica gel with 25% $CHCl_3$/hexane to give 637 mg of the sulfone and 3.073 g (8.24 mmoles, 60%) of the sulfoxide as a white solid. mp: 59.5°–63° C. Elemental analysis calculated for $C_9H_4OF_7SBr$: C: 28.97; H: 1.08; Found: C: 29.05; H: 1.28 . $^{19}F$ NMR ($CD_2Cl_2$): −81.0 (t, J=9 Hz, 3F), −112.4 (d of m, J=245 Hz, 1F), −124.0 (d of m, J=245 Hz, 1F), −124.8 (d, J=14 Hz, 2F).

EXAMPLE 1

(4-Fluorophenyl)Perfluorodecyl Sulfone

To a solution of 13.5 g (0.09 mol) of sodium 4-fluorobenzenethiolate (prepared from the thiol and sodium methoxide in methanol) in 500 mL of dimethylformamide was added 58.2 g (0.09 mol) of solid perfluorodecyl iodide. The solution was heated to 30° C. for 1 hr and 40° C. for 1 hr. After stirring overnight at room temperature, it was heated to 45° C. for 2 hr and poured into ice water. Ether was added, followed by sodium chloride, and the ether layer was separated. The aqueous solution was extracted with 2×300 mL of ether. The combined ether extracts were washed with 2×150 mL of saturated aqueous sodium chloride solution and concentrated on a rotary evaporator. The residue was distilled in a Kugelrohr apparatus at 73°–77° C. and 0.05 mm pressure to give 54.5 g (94%) of product,(4-fluorophenyl)perfluorodecyl sulfide, as a white solid.

$^1$H-NMR (CD$_2$Cl$_2$) δ 7.15(m, 2H); 7.65 (m, 2H).

$^{19}$F-NMR (CD$_2$Cl$_2$) δ −81.2 (3F); −87.5 (1F); −108.9 (2F); −119.4 (2F); −121.4 (2F); −121.9 (8F); −122.9 (2F); −126.4 (2F).

DSC analysis of another sample prepared in the same fashion showed a mp of 39° C.

ANAL. Calcd. for C$_{16}$H$_4$F$_{22}$S: C, 29.74; H, 0.62; F, 64.68; S, 4.96. Found: C, 29.61; H, 0.79; F, 64.49; S, 5.51.

The (4-fluorophenyl)perfluorodecyl sulfide prepared above (51.5 g, 0.08 mol) was dissolved in 500 mL of glacial acetic acid. Chromium trioxide (26 g, 0.26 mol) was added and the solution was heated at reflux for 4 hr. After cooling to room temperature, the solution was added to ice water and extracted with 10×500 mL of ether. The combined ether extracts were washed with saturated aqueous sodium chloride solution and saturated aqueous sodium bicarbonate solution, dried over MgSO$_4$, and concentrated to dryness. The residue was distilled in a Kugelrohr apparatus at 73° C. and 0.05 mm pressure to give 52 g of the product as a white solid, DSC mp 91.5° C.

$^1$H-NMR (CD$_2$Cl$_2$) δ 7.39 (m, 2H); 8.09 (m, 2H).

$^{19}$F-NMR (CD$_2$Cl$_2$) δ −81.2 (3F); −98.2 (1F); −111.5 (2F); −119.9 (2F); −121.8 (10F); −122.9 (2F); −126.4 (2F).

ANAL. Calcd. for C$_{16}$H$_4$F$_{22}$SO$_2$: C, 28.33; H, 0.59; F, 61.63; S, 4.73. Found: C, 28.65; H, 0.49; F, 61.10; S, 4.73.

The optical properties of this compound are shown for Compound Number 4 in Table 1.

EXAMPLE 2

(4-Diethylaminophenyl)Perfluorodecyl Sulfone

A mixture of 13.6 g (0.02 mol) of (4-fluorophenyl)-perfluorodecyl sulfone, prepared according to the procedure of Example 1, and 400 mL of dioxane was warmed to give a homogeneous solution and excess diethylamine (15 g) was added. The solution was warmed to 80° C. for 4 hr. An additional 10 g of diethylamine and 100 mL of dioxane were added and the solution was stirred overnight at 58° C. Glpc analysis still showed incomplete reaction, so the solution was heated for 8 hr at reflux. The solution was then evaporated to dryness and dissolved in a mixture of ether and water. The aqueous solution was extracted with ether. The combined ether extracts were dried and concentrated to dryness. The residue was recrystallized from hexane giving 11.4 g (80%) of product, mp 124°–125.5° C.

$^1$H-NMR (CD$_2$Cl$_2$) δ 1.22 (t, 6H); 3.45 (q, 4H); 6.75 (d, 2H); 7.75 (d, 2H).

$^{19}$F-NMR (CD$_2$Cl$_2$) −81.14 (3F); −112.7 (2F); −120.1 (2F); 121.8 (10F); −122.9 (2F); −126.3 (2F).

ANAL. Calcd. for C$_{20}$H$_{14}$F$_{21}$NO$_2$S: C, 32.54; H, 1.93; N, 1.92; F, 54.55; S, 4.38. Found: C, 32.70; H, 1.89; N, 1.87; F, 54.18; S, 4.75.

The optical properties of this compound are shown for Compound Number 3 in Table 1.

EXAMPLE 3

(4'-Methoxy-4-Biphenoxyphenyl)Perfluorodecyl Sulfone

A mixture of 3.00 g (15 mmol) of 4-methoxy-4'-hydroxybiphenyl, 2.81 g (20.3 mmol) of anhydrous potassium carbonate, 35 mL of DMAC and 35 mL of toluene was azeotropically distilled under argon until the pot temperature reached 135° C. The (4-fluorophenyl)perfluorodecyl sulfone, prepared according to the procedure of Example 1, (10.17 g, 15 mmol), was added and the mixture was stirred for 2.5 hr at 140° C. The cooled solution was poured into ice water and the solid collected. The solid was dissolved in ethyl acetate and concentrated to dryness, then slurried with benzene and concentrated. The residue was recrystallized from hot ethyl acetate to give in two crops 10.4 g (81%) of product, mp 176°–176.5° C.

$^1$H-NMR (CD$_2$Cl$_2$) δ 3.82 (s, 3H); 7.0 (d, 2H); 7.19 (d of d, 4H); 7.55 (d, 2H); 7.65 (d, 2H); 7.95 (d, 2H).

$^{19}$F-NMR (CD$_2$Cl$_2$) d −81.0 (3F); −111.8 (2F); −119.9 (2F); −121.7 (10F); −122.8 (2F); −126.2 (2F).

ANAL. Calcd. for C$_{29}$H$_{15}$F$_{21}$O$_4$S: C, 40.57; H, 1.76; F, 46.48; S, 3.73. Found: C, 40.67; H, 1.81; F, 46.59; S, 4.01

EXAMPLE 4

(4-Pentoxyphenyl)Perfluorodecyl Sulfone

Sodium metal (0.25 g) was added to 50 mL of 1-pentanol under nitrogen and allowed to dissolve. The (4-fluorophenyl)perfluorodecyl sulfone, prepared according to the procedure of Example 1, was added in two portions (4.0 g and 3.4 g, total of 0.011 mol), 1 hr apart, to the solution heated at 70° C. After the second addition the solution was heated for 6 hr. After cooling to room temperature, the solution was concentrated on a rotary evaporator and heated at 125° C. and 0.1 mm to remove any unreacted 1. The residue was dissolved in ether, filtered, concentrated to dryness and recrystallized from hexane to give 6.25 g (77%) of white needles, mp 96°–96.5° C.

$^1$H-NMR (CD$_2$Cl$_2$) δ 0.94 (t, 3H); 1.42 (m, 4H); 1.84 (q, 2H); 4.08 (t, 2H); 7.10 (d, 2H); 7.92 (d, 2H).

$^{19}$F-NMR (CD$_2$Cl$_2$) δ −81.14 (3F); −112.2 (2F); −120.1 (2F); −121.8 (10F); −122.9 (2F); −126.3 (2F).

ANAL. Calcd. for C$_{21}$H$_{15}$F$_{21}$O$_3$S: C, 33.79; H, 2.03; F, 53.46; S, 4.30. Found: C, 33.63; H, 1.93; F, 53.86; S, 4.67

EXAMPLE 5

[4-(2-Methylbutoxy)phenyl]Perfluorodecyl Sulfone

Sodium metal (0.42 g) was added to 100 mL of freshly distilled (−) 2-methyl-1-butanol ([α]$_D$=−6.1°) and stirred until dissolved. The (4-fluorophenyl)-perfluorodecyl sulfone, prepared according to the procedure of Example 1, (12.3 g, 0.018 mol) was added and the resulting solution was stirred at 68° C. for 2.5 hr. The solution was concentrated on a rotary evaporator at temperatures up to 105° C. and 0.05 mm. The residue was recrystallized from hexane giving 4.52 g (33%) of white solid, mp 96°–97° C., [α]$_D$ (Isooctane)=+2.9°.

$^1$H-NMR (CD$_2$Cl$_2$) δ 0.95 (m, 3H); 1.04 (m, 3H); 1.3–2.0 (m, 3H); 3.90 (m, 2H); 7.11 (d, 2H); 7.95 (d, 2H).

$^{19}$F-NMR (CD$_2$Cl$_2$) δ −81.2 (3F); −112.2 (2F); −120.0 (2F); −121.8 (10F); −122.9 (2F); −126.4 (2F).

ANAL. Calcd. for $C_{21}H_{15}F_{21}O_3S$: C, 33.79; H, 2.03; F, 53.46; S, 4.30. Found: C, 34.29; H, 2.04; F, 52.76; S, 4.74

The optical properties of this compound are shown for Compound Number 2 in Table 1.

EXAMPLE 6

Reaction of (4-Fluorophenyl)Perfluorodecyl Sulfone with L-Prolinol

Two grams (2.95 mmoles) of (4-fluorophenyl)-perfluorodecyl sulfone and 0.30 g (2.95 mmoles) of L-prolinol and 0.42 g (3.04 mmoles) of $K_2CO_3$ were placed in about 40 ml of dimethylsulfoxide. The resulting slurry was heated in an oil bath at 50° C. for two days. Water was added and the white solid was filtered and washed with water. Thus obtained was 2.195 g of the product.

SHG: 0.017×urea.

$^1$H-NMR ($CD_2Cl_2$) 7.8 (d, 2H); 6.8 (d, 2H); 4.0 (m, 1H); 3.6 (m, 3H); 3.3 (m, 1H); 2.5 (s, 1H); 2.0 (m, 4H).

EXAMPLE 7

4-Methoxy-4'-Perfluorohexylsulfonylstilbene 0.600 g (1.11 mmoles) of (4-bromophenyl)-perfluorohexyl sulfone, 0.160 g (1.19 mmoles) of vinyl anisole, 20 mg of $Pd(OAc)_2$ and 20 mg $P(o\text{-}tolyl)_3$ were placed in 10 ml of n-tributyl amine and heated under nitrogen at 110° C. overnight. Saturated $NH_4Cl$ solution was added and the mixture extracted with 3×50 ml of $CH_2Cl_2$, dried over $MgSO_4$. After removing the solvent by rotary evaporation, the residue was purified by flash chromatography. Thus obtained was 0.241 g (0.40 mmoles, 36.6%). Elemental analyses for : Found: C: 42.04, 41.84; H: 2.13, 2.06; calculated for $C_{21}H_{13}F_{13}SO_3$: C: 42.58; H: 2.21. High resolution mass spectrum: measured: 592.0474; calculated: 592.0378. $^1$H nmr ($CD_2Cl_2$): trans isomer: 7.97 (d, J=8.6 Hz, 2H), 7.75 (d, J=8.6 Hz, 2H), 7.53 (d, J=8.7 Hz, 2H), 7.34 (d, J=116.3 Hz, 1H), 7.06 (d, J=116.3 Hz, 1H), 6.94 (d, J=8.7 Hz, 2H), 3.84 (s, 3H). cis isomer: 8.18 (d, J=8.4 Hz, 2H), 7.86 (d, J=8.4 Hz, 2H), 7.13 (d, J=8.7 Hz, 2H), 6.80 (d, J=112.2 Hz, 1H), 6.77 (d, J=8.7 Hz, 2H), 6.55 (d, J=112.2 Hz, 1H), 3.79 (s, 3H). $^1$H nmr indicates a 10:1 mixture of trans to cis isomers. SHG: inactive.

The optical properties of this compound are shown for Compound Number 15 in Table 3.

EXAMPLE 8

4-Methoxy-4'Perfluoropropylsulfonylstilbene

The procedure of Example 7 was followed except 0.600 g (1.54 mmoles) of (4-bromophenyl)perfluoropropyl sulfone and 0.207 g (1.54 mmoles) of vinyl anisole in 10 ml of $N(n\text{-}Bu)_3$ were heated under nitrogen at 110° C. overnight. Isolation of product gave 0.337 g (0.76 mmoles, 49.4%) of the product as a light yellow solid. Elemental analysis: Found: C: 49.09; H: 2.92; calculated for $C_{18}H_{13}F_7SO_2$: C: 48.87; H: 2.96. $^1$H nmr indicates a mixture of trans and cis isomer with the ratio of trans/cis being 4.7. $^1$H nmr ($CD_2Cl_2$): trans isomer: 7.97 (d, J=8.5 Hz, 2H), 7.75 (d, J=8.5 Hz, 2H), 7.54 (d, J=8.8 Hz, 2H), 7.34 (d , J=116.3 Hz, 1H), 7.05 (d, J=116.3 Hz, 1H), 6.95 (d, J=8.8 Hz, 2H), 3.85 (s, 3H). cis isomer: 7.86 (d, J=8.5 Hz, 2H), 7.8 (masked by trans isomer, 2H), 7.14 (d, J=8.7 Hz, 2H), 6.81 (d, J=112.1 Hz, 1H), 6.79 (d, J=8.77 Hz, 2H), 6.55 (d, J=112.1 Hz, 1H), 3.80 (s, 3H). SHG: 0.06×urea.

EXAMPLE 9

4-Methoxy-4'-Perfluoropropylsulfonylbiphenyl

To 600 mg (1.54 mmole) of (4-bromophenyl)-perfluoropropyl sulfone was dissolved in 10 ml of toluene and 329 mg (0.285 mmole) of $Pd(PPh_3)_4$ (one can use as little as 40 mg of catalyst). The mixture was stirred for 10 minutes and then 234 mg (1.54 mmole) of 4-methoxyphenylboronic acid in 4 ml of methanol was added. To this mixture was then added 326 mg (3.08 mmole) of $Na_2CO_3$ in 2 ml of water. The mixture was then stirred at 80° C. overnight. Brine was added and the mixture extracted with 3×50 ml of $CH_2Cl_2$, dried over $MgSO_4$, and solvent removed by rotary evaporation. The residue was flash chromatographed (silica gel, $CHCl_3$) to give 542 mg of the desired product (1.30 mmoles, 84.5%). SHG: not active. Elemental analyses: calculated for $C_{16}H_{11}F_7O_3S$: C: 46.16; H: 2.66; Found: C: 46.06; H: 2.62. mp: 78.5°–80.5° C. $^1$Hnmr ($CD_2Cl_2$): 8.06 (d, J=8.6 Hz, 2H), 7.86 (d, J=8.6 Hz, 2H), 7.64 (d, J=8.8 Hz, 2H), 7.05 (d, J=8.8 Hz, 2H), 3.87 (s, 3H).

The optical properties of this compound are shown for Compound Number 11 in Table 2.

EXAMPLE 10

4-Methoxy-4'-Perfluorohexylsulfonylbiphenyl

In 10 ml of toluene was added 600 mg (1.11 mmoles) of (4-bromophenyl)perfluorohexyl sulfone, and 20 mg (0.17 mmoles) of $Pd(PPh_3)_4$. To this clear colorless solution was added 170 mg (1.12 mmoles) of 4-methoxyphenylboronic acid in 2 ml of methanol, 240 mg (2.26 mmoles) of $Na_2CO_3$ in 1 ml of water. The mixture was stirred under nitrogen at 80° C. overnight. Isolation in accordance with the procedure of Example 9 gave after flash chromatography (silica gel, 50% $CHCl_3$/hexane) 343 mg of the biphenyl (0.60 mmoles, 54.6%). Elemental analyses: Found: C: 40.29; H: 2.03; calculated for $C_{19}H_{11}F_{13}O_3S$: C: 40.30; H: 1.96 Mp: 101.5°–103° C. SHG: not active. $^1$H nmr ($CD_2Cl_2$): 8.05 (d, J=8.6 Hz, 2H), 7.87 (d, J=8.6Hz, 2H), 7.65 (d, J=8.8 Hz, 2H), 7.04 (d, J=8.8 Hz, 2H), 3.87 (s 3H).

The optical properties of this compound are shown for Compound Number 12 in Table 2.

EXAMPLE 11

4-N,N-Dimethylamino-4'-Perfluorohexylsulfonylbiphenyl

In 10 ml of toluene was added 600 mg (1.11 mmoles) of 4-(4-bromophenyl)perfluorohexyl sulfone, and 20 mg (0.17 mmoles) of $Pd(PPh_3)_4$. To this clear colorless solution was added 250 mg (1.52 mmoles) of 4-N,N-dimethylaminophenylboronic acid in 2 ml of methanol, 240 mg (2.26 mmoles) of $Na_2CO_3$ in 1-2 ml of water. The mixture was stirred under nitrogen at 80° C. overnight. Isolation in accordance with the procedure of Example 9 gave after flash chromatography (silica gel, 50% $CHCl_3$/hexane) 237 mg of the biphenyl (0.41 mmoles, 36.8%). Elemental analyses: Found: C: 41.54; H: 2.48; calculated for $C_{20}H_{14}F_{13}NO_2S$: C: 41.46; H: 2.44. Mp: 138°–140° C. SHG: not active. 1H nmr ($CD_2Cl_2$): 7.99 (d, J=8.6 Hz, 2H), 7.84 (d, J=8.6 Hz, 2H), 7.62 (d, J=9.0 Hz, 2H), 6.81 (d, J=9.0 Hz, 2H), 3.03 (s 3H).

EXAMPLE 12

4-(4-N,N-Dimethylaminophenoxyl) Phenylperfluorodecyl Sulfone

To 50 ml of dimethylsulfoxide was added 202 mg (1.47 mmole) of 4-N,N-dimethylaminophenol, 1.0 g (1.47 mmoles) 4-(4-fluorophenyl)perfluorodecylsulfone, and 202 mg (1.90 mmole) of $K_2CO_3$. The mixture was heated at 50° C. overnight and then washed with water and vacuum dried. The white solid was dissolved in chloroform to remove insolubles and then the solvent removed by rotary evaporation to give 967 mg (1.21 mmoles, 82.7%) the desired product. The material can be recrystallized from $CHCl_3$/hexane. Elemental analyses: Found: C: 36.09; H: 1.79; calculated for $C_{24}H_{14}NO_3F_{21}S$: C: 36.24; H: 1.77. Mp: 121°–124° C. SHG: not active. $^1H$ nmr ($CD_2Cl_2$): 7.91 (d, J=8.8 Hz, 2H), 7.10 (d, J=8.8 Hz, 2H), 6.99 (d, J=8.5 Hz, 2H), 6.76 (d, J=8.8 Hz, 2H), 2.96 (s, 6H).

EXAMPLE 13

4-Pyrrolidonophenylperfluorodecyl Sulfone

To 40 ml of dimethylsulfoxide was added 105 mg (1.47 mmole) of pyrrolidine, 1.0 g (1.47 mmoles) 4-(4-fluorophenyl)perfluorodecylsulfone, and 210 mg (1.52 mmole) of $K_2CO_3$. The mixture was heated at 50° C. overnight and then treated with water. The solid was filtered, washed with water and vacuum dried to give 790 mg (1.08 mmoles, 73.7%) of the product. Elemental analyses: Found: C: 32.78; H: 1.63; calculated for $C_{20}H_{12}NO_2F_{21}S$: C: 32.94; H: 1.66. Mp: 151°–153° C. SHG: not active. $^1H$ nmr ($CD_2Cl_2$): doublets at 7.75 and 6.63 ppm and multiplets at 3.4 and 2.1 ppm.

EXAMPLE 14

4-(2,6-Dimethylphenoxyl)Phenylperfluorodecyl Sulfone

To 30 ml of dimethylsulfoxide was added 180 mg (1.47 mmole) of 2,6-dimethylphenol, 1.0 g (1.47 mmoles) 4-(4-fluorophenyl)perfluorodecylsulfone, and 210 mg (1.52 mmole) of $K_2CO_3$. The mixture was heated at 50° C. overnight and then washed with water and vacuum dried. The white solid was dissolved in chloroform to remove insolubles and then the solvent removed by rotary evaporation to give 1.162 g (1.47 mmoles, 100%) of the desired product. It was recrystallized from hot hexane. Elemental analyses: Found: C: 37.20; H: 1.55; calculated for $C_{24}H_{13}F_{21}O_3S$: C: 36.94; H: 1.68. Mp: 134°–136.5° C. SHG: not active. $^1H$ nmr ($CD_2Cl_2$): 7.95 (d, 2H), 7.18 (s, 3H), 6.99 (d, 2H), 2.10 (s, 6H).

EXAMPLE 15

4-(4-Thiophenoxyl)Phenylperfluorodecyl Sulfone

To 30 ml of dimethylsulfoxide was added 200 mg (1.51 mmole) of sodium thiophenoxide, and 1.0 g (1.47 mmoles) of 4-(4-fluorophenyl)perfluorodecylsulfone. The mixture was heated at 50° C. overnight and then washed with water and vacuum dried. The white solid was dissolved in chloroform to remove insolubles and then the solvent removed by rotary evaporation to give 953 mg (1.24 mmoles, 84.4%) of the desired product. It was recrystallized from hot hexane. Elemental analyses: Found: C: 34.11; H: 1.25; calculated for $C_{22}H_9F_{21}O_2S_2$: C: 34.39; H: 1.18. Mp: 122°–123.5° C. SHG: not active. $^1H$ nmr ($CD_2Cl_2$): 7.8 (d, 2H), 7.6 (m, 2H), 7.5 (m,3H), 7.3 (d, 2H).

EXAMPLE 16

4-(4-Methoxyphenoxyl)Phenylperfluorodecyl Sulfone

To 30 ml of dimethylsulfoxide was added 182 mg (1.47 mmole) of 4-methoxyphenol, 1.0 g (1.47 mmoles) of 4-(4-fluorophenyl)perfluorodecylsulfone and 210 mg (1.52 mmoles) of $K_2CO_3$. The mixture was heated at 50° C. overnight and then washed with water and vacuum dried. The white solid was dissolved in chloroform to remove insolubles and then the solvent removed by rotary evaporation to give 1.056 g (1.35 mmoles, 91.8%) of the desired product. It was recrystallized from hot hexane. Elemental analyses: Found: C: 35.52; H: 1.13; calculated for $C_{23}H_{11}F_{21}O_4S$: C: 35.52; H: 1.42. Mp: 137°–139° C. SHG: not active. $^1H$ nmr ($CD_2Cl_2$): 7.9 (d, 2H), 7.15 (d, 2H), 7.1 (d,2H), 6.99 (d, 2H), 3.8 (s,3H).

The optical properties of this compound are shown for Compound Number 16 in Table 4.

EXAMPLE 17

4-(4-Methoxythiophenoxyl)Phenylperfluorodecyl Sulfone

To 30 ml of dimethylsulfoxide was added 152 mg (1.47 mmole) of 4-methoxythiophenol, 1.0 g (1.47 mmoles) of 4-(4-fluorophenyl)perfluorodecylsulfone and 210 mg (1.52 mmoles) of $K_2CO_3$. The mixture was heated at 50° C. overnight and then washed with water and vacuum dried to give 1.092 g (1.37 mmoles, 93%) of the desired product as an off white solid. It was recrystallized from hot hexane. Elemental analyses: Found: C: 35.95, 35.97; H: 1.16, 1.46; calculated for $C_{23}H_{11}F_{21}O_3S_2$: C: 34.60; H: 1.39. Mp: 122°–123.5° C. SHG: not active. $^1H$ nmr ($CD_2Cl_2$): 7.8 (d, 2H), 7.5 (d, 2H), 7.23 (d,2H), 7.05 (d, 2H), 3.9 (s,3H). HRMS: Found: 798.0267; calculated: 797.9814.

The optical properties of this compound are shown for Compound Number 17 in Table 4.

EXAMPLE 18

Reaction of L-Prolinol with 4-(4-Fluorophenyl)Perfluoropropyl Sulfone

To 30 ml of dimethylsulfoxide was added 308 mg (3.034 mmole) of L-prolinol, 1.0 g (3.04 mmoles) of 4-(4-fluorophenyl)perfluoropropylsulfone and 425 mg (3.07 mmoles) of $K_2CO_3$. The mixture was heated at 50° C. overnight and then washed with water and vacuum dried to give 976 mg (2.38 mmoles, 78.4%) of the desired product as an off white solid. It was recrystallized from hot hexane. Elemental analyses: Found: C: 41.08; H: 3.45; calculated for $C14H_{14}F_7O_3NS$: C: 41.08; H: 3.44. Mp: 80°–83° C. SHG: not active. $^1H$ nmr ($CD_2Cl_2$): 7.8 (d, 2H), 6.8 (d, 2H), 4.03 (m, 1H), 3.7 (m, 1H), 3.6 (m, 1H), 3.5 (m, 1H), 3.3 (m, 1H), 2.6 (s, 1H), 2.1 (m, 4H).

EXAMPLE 19

Reaction of Piperazine with 4-(4-Fluorophenyl)Perfluoropropyl Sulfone

To 30 ml of dimethylsulfoxide was added 127 mg (1.47 mmole) of piperazine, 1.0 g (1.47 mmoles) of 4-(4-fluorophenyl)perfluoropropylsulfone and 210 mg (1.52 mmoles) of $K_2CO_3$. The mixture was heated at 50° C. overnight and then washed with water and vacuum dried to give 1.084 g (1.46 mmoles, 99%) of the desired product as a white solid. It was recrystallized from hot hexane. Elemental analyses: Found: C: 33.03, 33.33; H: 1.56, 1.86; calculated for $C_{20}H_{13}F_{21}O_2N_2S$: C: 32.27; H: 1.76. SHG: not active. HRMS: Found: 744.062; calculated: 744.0362. $^1H$ nmr ($CD_2Cl_2$): 7.8 (d, 2H), 6.9 (d, 2H), 3.4 (m, 4H), 2.9 (m, 4H), 1.6 (s, 1H).

EXAMPLE 20

4-(4-Acetamidothiophenoxy)Phenylperfluorodecyl Sulfone

To 30 ml of dimethylsulfoxide was added 246 mg (1.47 mmole) of 4-acetamidothiophenol, 1.0 g (1.47 mmoles) of 4-(4-fluorophenyl)perfluorodecylsulfone and 406 mg (2.94 mmoles) of $K_2CO_3$. The mixture was heated at 50° C. overnight and then washed with water and vacuum dried to give 1.202 g (1.45 mmoles, 99%) of the desired product as an off white solid. Elemental analyses: Found: C: 34.99; H: 1.72; calculated for $Cl_{14}H_{14}F_7O_3NS$: C: 34.92; H: 1.47. Mp: 178.5°–182° C. SHG: 0.2×urea. $^1H$ nmr (THF-$D_8$): 9.40 (s, 1H), 7.86 (d, J=8.7 Hz, 2H), 7.79 (d, J=8.7 Hz, 2H), 7.50 (d, J=8.7 Hz, 2H), 7.32 (d, J=8.7 Hz, 2H), 2.07 (s, 3H).

EXAMPLE 21

4-(4-Acetamidophenoxy)Phenylperfluorodecyl Sulfone

To 30 ml of dimethylsulfoxide was added 233 mg (1.47 mmole) of 4-acetamidophenol, 1.0 g (1.47 mmoles) of 4-(4-fluorophenyl)perfluorodecylsulfone and 406 mg (2.94 mmoles) of $K_2CO_3$. The mixture was heated at 50° C. overnight and then washed with water and vacuum dried to give 1.101 g (1.36 mmoles, 92.5%) of the desired product as a white solid. Elemental analyses: Found: C: 35.72; H: 1.67; calculated for $C_{24}H_{12}F_{21}O_4NS$: C: 35.62; H: 1.49. Mp: 127°–128° C. SHG: not active. $^1H$ nmr (THF-$d_8$): 9.20 (s, 1H), 8.01 (d, J=9.0 Hz, 2H), 7.73 (d, J=9.0 Hz, 2H), 7.21 (d, J=9.0 Hz, 2H), 7.07 (d, J=9.0 Hz, 2H), 2.07 (s, 3H).

EXAMPLE 22

4-(4-Acetamidophenoxy)Phenylperfluoropropyl Sulfone

To 30 ml of dimethylsulfoxide was added 461 mg (3.05 mmole) of 4-acetamidophenol, 1.0 g (3.05 mmoles) of 4-(4-fluorophenyl)perfluoropropylsulfone and 843 mg (6.10 mmoles) of $K_2CO_3$. The mixture was heated at 50° C. overnight and then washed with water and vacuum dried to give 740 mg (1.62 mmoles, 53.1%) of the desired product as a white solid. Elemental analyses: Found: C: 44.44; H: 2.84; calculated for $C_{17}H_{12}F_7O_4NS$: C: 44.45; H: 2.63. Mp: 159.5°–162° C. SHG: 0.14×urea. $^1H$ nmr ($CD_2Cl_2$): 7.94 (d, J=9.0 , 2H), 7.61 (d, J=8.9 Hz, 2H), 7.28 (s, 1H), 7.14 (d, J=9.0 Hz, 2H), 7.09 (d, J=8.9 Hz, 2H), 2.15 (s, 3H).

EXAMPLE 23

4-(4-Acetamidothiophenoxy)Phenylperfluorodecyl Sulfone

To 30 ml of dimethylsulfoxide was added 570 mg (3.05 mmole) of 4-acetamidothiophenol, 1.0 g (3.05 mmoles) of 4-(4-fluorophenyl)perfluoropropylsulfone and 843 mg (6.10 mmoles) of $K_2CO_3$. The mixture was heated at 50° C. overnight and then washed with water and vacuum dried to give 1.196 g (2.51 mmoles, 82.5%) of the desired product as an off white solid. Elemental analyses: Found: C: 42.70; H: 2.81; calculated for $C_{17}H_{12}F_7O_3NS_2$: C: 42.95; H: 2.54. SHG: 1.1×urea. $^1H$ nmr ($CD_2Cl_2$): 7.78 (d, J=8.6 Hz, 2H), 7.66 (d, J=8.6 Hz, 2H), 7.53 (d, J=8.6 Hz, 2H), 7.39 (s, 1H), 7.26 (d, J=8.6 Hz, 2H), 2.18 (s, 3H).

EXAMPLE 24

4-(4-Aminophenoxy)Phenylperfluoropropyl Sulfone

To 666 mg (1.45 mmoles) of 4-(4-amidophenoxy)phenylperfluoropropyl sulfone was added 10 ml of concentrated HCl and 10 ml of ethanol. The mixture was refluxed for 2 hours and 20 ml of water was added to the cooled solution. The mixture was neutralized with 1M NaOH. A white precipitate formed which was filtered, washed with water and vacuum dried to give 593 mg (1.42 mmoles, 98.0%) of the desired product as an off white solid. SHG: not active. $^1H$ nmr ($CD_2Cl_2$): 7.91 (d, J=9.0, 2H), 7.10 (d, J=9.0 Hz, 2H), 6.90 (d, J=8.7 Hz, 2H), 6.73 (d, J=8.7 Hz, 2H), 3.776 (s, 2H).

EXAMPLE 25

4-(4-Aminothiophenoxy)Phenylperfluoropropyl Sulfone

To 1.009 g (2.12 mmoles) of 4-(4-amidothiophenoxy)phenylperfluoropropyl sulfone was added 10 ml of concentrated HCl and 10 ml of ethanol. The mixture was refluxed for 2 hours and 20 ml of water was added to the cooled solution. The mixture was neutralized with 1M NaOH. A white precipitate formed which was filtered, washed with water and vacuum dried to give 904 mg (2.09 mmoles, 98.4%) of the desired product as a white solid. SHG: not active. Elemental analyses: Found: C: 41.27; H: 2.52; calculated for $C_{15}H_{10}NO_2F_7S_2$: C: 41.57; H: 2.33. $^1H$ nmr ($CD_2Cl_2$): 7.78 (d, 2H), 7.38 (d, 2H), 7.2 (d, 2H), 6.78 (d, 2H), 4.05 (s, 2H).

EXAMPLE 26

Pt(PEt$_3$)$_2$(Br)(p-Perfluoropropylsulfonylphenyl)

To 500 mg (0.749 mmoles) of Pt(PEt$_3$)$_4$ in 50 ml of toluene was added 4-bromoperfluoropropylphenyl sulfone in 30 ml of toluene. The mixture was stirred overnight. The solvent from the colorless solution was removed by rotary evaporation and the solid washed with hexane. Thus obtained was 313 mg (0.422 mmoles, 56.4%) of the desired product. SHG: 0.45×urea. $^1H$ nmr ($CD_2Cl_2$): 7.76 (d, J=8.5, $J_{Pt}$=65.4 Hz, 2H), 7.48 (d with unresolved coupling with Pt, J=8.4 Hz, 2H), 1.7 (m, 12 H), 1.2 (m, 18 H). $^{31}P$ nmr ($CD_2Cl_2$): 13.025 (s, $J_{Pt}$=2649 Hz,). X-ray structure determined to be R3.

EXAMPLE 27

Reaction of Pyrrolidine with p-F-$C_6H_4S(C_{10}F_{21})$=$NSO_2CF_3$

In about 11 mL of dimethyl sulfoxide was added 0.032 g (0.45 mmoles) of pyrrolidine, 0.070 g (0.51 mmoles) of $K_2CO_3$ and 0.357 g (0.45 mmoles) of p-F-$C_6H_4S(C_3F_7)$=$NSO_2CF_3$. The mixture was heated at 50° C. overnight. The mixture was added to water and the product filtered and washed with water. Thus obtained was 0.336 g (0.40 mmoles, 88%) of the desired product. Elemental analysis calculated for $C_{21}H_{12}N_2O_2F_{24}S_2$: C: 29.87, H: 1.43; Found: C: 29.80, H: 1.57. $^1H$ NMR ($CD_2Cl_2$): 7.69 (d, J=9.1 Hz, 2H), 6.71 (d, J=9.1 Hz, 2H), 3.40 (m, 4H), 2.05 (m, 4H). $^{19}F$ NMR ($CD_2Cl_2$): −78.7 (s, 3F), −80.9 (t, J=110 Hz, 3F), −106 (d of t, J=10, 223 Hz, 1F), −111 (d of t, J=110, 223 Hz, 2F), −118.5 (s, 2F), −121.8 (s, 10F), −122.7 (s, 2F), −126.3 (s, 2F). SHG: inactive. $\lambda_{max}$(p-dioxane)=336 nm, $\mu$=9, and $\beta$=113×10$^{-30}$ esu.

EXAMPLE 28

4-Methoxy-4'-S-perfluoropropyl-N-trifluoromethylsulfonylsulfimide biphenyl

To 10 mL of toluene was added 0.500 g (0.992 moles) of S-perfluoropropyl-S-4-bromophenyl-N-trifluoromethylsulfonylsulfimide. To this mixture was added 60 mg (0.052 mmoles) of Pd(PPh$_3$)$_4$ in 5 mL of toluene. The mixture was stirred for 10 minutes and then 0.151 g (0.992 mmoles) of 4-methoxyphenylboronic acid in 4 mL of MeOH was added. To this mixture was added 0.21 g (1.98 mmoles) of Na$_2$CO$_3$ in 2 mL of water. The slurry was heated at 100° C. overnight. To the cooled mixture was added 50 mL of saturated aqueous solution of NaCl and extracted 3 times with 75 mL of CH$_2$Cl$_2$. The organic layer was dried over MgSO$_4$, solvent removed by rotary evaporation and the residue chromatographed with 50% CHCl$_3$/hexane. Thus obtained was 0.240 g (0.45 mmoles, 45%) of the desired product as an off-white solid. Elemental analysis calculated for C$_{17}$H$_{11}$NO$_3$F$_{10}$S$_2$: C: 38.43; H: 2.09; Found: C: 39.23, 39.03; H: 1.86, 1.77. $^1$H NMR (CD$_2$Cl$_2$): 7.99 (d, J=8.6 Hz, 2H), 7.91 (d, J=8.6 Hz, 2H), 7.63 (d, J=8.7 Hz, 2H), 7.04 (d, J=8.7 Hz, 2H), 3.87 (s, 3H). $^{19}$F NMR (CD$_2$Cl$_2$): −78.4 (s, 3F), −80.6 (t, J=9 Hz, 3F), −104.5 (d of q, J=221, 9 Hz, 1F), −110.6 (d of m, J=221 Hz, 1F), −122.5 (s, 2F). SHG: inactive. $\lambda_{max}$(p-dioxane)=320 nm, $\mu$=7.9, and $\beta$=9.4×10$^{-30}$ esu.

EXAMPLE 29

Reaction of (S)-(+)-2-pyrrolidinemethanol with p-F-C$_6$H$_4$S(C$_3$F$_7$)=NSO$_2$CF$_3$ The procedure of Example 27 was followed except using 300 mg (0.677 mmoles) of p-F-C$_6$H$_4$S(C$_3$F$_7$)=NSO$_2$CF$_3$, 69 mg (0.677 mmoles) of (S)-(+)-2-pyrrolidinemethanol, and 100 mg (0.724 mmoles) of K$_2$CO$_3$. After workup, obtained 0.174 g (0.33 mmoles, 49%) of the desired product as an off-white solid. Elemental analysis calculated for C$_{15}$H$_{14}$N$_2$O$_3$F$_{10}$S$_2$: C: 34.36; H: 2.69; Found: C: 34.54; H: 2.62. $^{19}$F NMR (CD$_2$Cl$_2$): −78.7 (s, F), −80.7 (t, J=9 Hz, 3F), −106.5 (d of m, J=223 Hz, 1F), −112.2 (d of m, J=223 Hz, 1F), −123.0 (d, J=9 Hz, 2F). SHG: inactive.

EXAMPLE 30

Reaction of diethylamine with p-F-C$_6$H$_4$S(C$_3$F$_7$)=NSO$_2$CF$_3$

The procedure of Example 27 was followed except using 310 mg (0.700 mmoles) of p-F-C$_6$H$_4$S(C$_3$F$_7$)=NSO$_2$CF$_3$, 51 mg (0.700 mmoles) of diethylamine, and 100 mg (0.72 mmoles) of K$_2$CO$_3$ in DMSO. The mixture was added to 50 mL of water. A gummy mass formed. Some saturated NH$_4$Cl was added and the mixture extracted with ether. The organic layer was dried over Na$_2$SO$_4$ and then the solvent removed. The residue was passed through silica gel with CHCl$_3$ to yield 102 mg (0.20 mmoles, 29%) of the desired product as a tan solid. Elemental analysis calculated for C$_{14}$H$_{14}$N$_2$O$_2$F$_{10}$S$_2$: C: 33.88; H: 2.84; Found: C: 33.67, 33.73; H: 3.34, 3.05. $^1$H NMR (CH$_2$Cl$_2$): 7.7 (d, 2H), 6.8 (d, 2H), 3.4 (q, 4H), 1.1 (t, 6H), $^{19}$F NMR (CD$_2$Cl$_2$): −78.7 (s, 3F), −80.8 (t, J=9 Hz, 3F), −106.6 (d of d of q, J=223, 9, 3 Hz), −112.4 (d of m, J=223 Hz, 1F), −123.0 (d, J=110 Hz, 2F). SHG: inactive. $\lambda_{max}$ (CD$_2$Cl$_2$)=338 nm.

EXAMPLE 31

Reaction of pyrrolidine with p-F-C$_6$H$_4$S(C$_3$F$_7$)=NSO$_2$CF$_3$

The procedure of Example 27 was followed except using 400 mg (0.902 mmoles) of p-F-C$_6$H$_4$S(C$_3$F$_7$)=NSO$_2$CF$_3$, 64 mg (0.902 mmoles) of pyrrolidine, and 125 mg (0.910 mmoles) of K$_2$CO$_3$. The workup was the same as Example 1 to give 385 mg (0.779 mmoles, 86%) of the desired product as a light yellow solid. Elemental analysis calculated for C$_{14}$H$_{12}$N$_2$O$_2$F$_{10}$S$_2$: C: 34.01; H: 2.45; Found: C: 33.88; H: 2.69. $^1$H NMR (CD$_2$Cl$_2$): 7.68 (d, J=9 Hz, 2H), 6.70 (d, J=9.2 Hz, 2H), 3.4 (m, 4H), 2.1 (m, 4H). $^{19}$F NMR (CD$_2$Cl$_2$): −78.7 (s, 3F), −80.8 (t, J=8.9 Hz, 3F); −106.8 (d of d of q, J=224, 9, 2 Hz, 1F), −112.2 (d of m, J=224, 1F), −123.0 (d, J=110 Hz, 2F). $\lambda_{max}$ (p-dioxane)=336 nm, $\mu$−10.2 and $\beta$=113×10$^{-30}$ esu.

EXAMPLE 32

Measurement of Optical Properties

Solutions of the compounds shown in Tables 1–4 were prepared in concentrations from 1×10$^{-3}$ molar to 7×10$^{-3}$ molar in the solvents shown in the Tables. For each compound, four solutions of graded concentrations, typically 1×10$^{-3}$ molar, 2×10$^{-3}$ molar, 3×10$^{-3}$ molar, and 4×10$^{-3}$ molar, were made. Physical measurements were carried out on all four solutions and the pure solvent. Densities were determined using an Anton Paar DMA45 calculating digital density meter. Capacitances were determined with a Kahl Scientific solution capacitance cell and a Hewlett Packard 4275A multi-frequency LCR meter. Refractive indexes at 589.3 nm and 633 nm were determined with a Precision Instruments refractometer. The nonlinear optical properties of the solutions shown in Tables 1–4 were determined using electric field induced second harmonic generation and third harmonic generation measurements described earlier and depicted in FIG. 1. For EFISH measurements, a pulsed electric field of about 20 kv/cm was used. From the measured solution properties, using Onsager local fields, the various molecular properties were calculated at the infinite dilution limit.

The results are shown in Tables 1 to 4. Compounds useful in the practice of this invention are shown by Compound Numbers, while comparative compounds are indicated by a "C" before the Compound Number. In all Tables $\mu$, $\alpha$, $\beta$, and $\gamma$ are in electrostatic units (esu) and the term Me=CH$_3$; Ph=C$_6$H$_5$; Bu=C$_4$H$_9$; Et=C$_2$H$_5$; Hex=C$_6$H$_{10}$; and p-Diox=p-dioxane.

TABLE 1

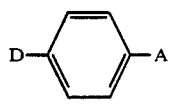

| Compound Number | A | D | solvent | $\lambda_{max}$ (nm) | $\mu$ $10^{-18}$ | $\alpha$ $10^{-23}$ | $\beta$ $10^{-30}$ | $\gamma$ $10^{-36}$ |
|---|---|---|---|---|---|---|---|---|
| C-1 | SO$_2$Me | OH | p-Diox | 290 | 3.4 | 1.7 | 1.3 | 3.0 |
| C-2 | SO$_2$C$_{16}$H$_{33}$ | NH$_2$ | CHCl$_3$ | 262 | 5.5 | 6.2 | 2.1 | 10 |
| C-3 | SO$_2$F | NH$_2$ | p-Diox | 274 | 6.0 | 1.7 | 3.0 | 2.5 |
| C-4 | SO$_2$C$_2$ClF$_3$H | N$_2$H$_3$ | p-Diox | 312 | 5.8 | 2.6 | 5.6 | −5 |
| C-5 | SO$_2$C$_6$F$_{13}$ | Me | p-Diox | 232 | 5.4 | 3.1 | 2 | 4.7 |
| 1 | SO$_2$C$_{10}$F$_{21}$ | OPh | CHCl$_3$ | 253 | 7.2 | 4.6 | 9.1 | −13 |
| 2 | SO$_2$C$_{10}$F$_{21}$ | OMeBu | CHCl$_3$ | 290 | 7.1 | 4.7 | 6.9 | −53 |
| 3 | SO$_2$C$_{10}$F$_{21}$ | NEt$_2$ | CHCl$_3$ | 314 | 7.6 | 4.6 | 13 | −15 |
| 4 | SO$_2$C$_{10}$F$_{21}$ | F | CHCl$_3$ | 225 | 4.3 | 3.8 | 1.5 | 5 |
| 5 | SO$_2$C$_{10}$F$_{21}$ | Br | CHCl$_3$ | 245 | 3.8 | 2.7 | 3.6 | 4 |
| C-6 | COH | Me | Neat |  | 3.0 | 1.6 | 1.7 | 6.5 |
| C-7 | COH | OPh | Neat | 269 | 2.8 | 2.5 | 1.9 | 12 |
| C-8 | COH | OMe | Neat | 269 | 3.5 | 1.7 | 2.2 | 7.7 |
| C-9 | COH | SMe | Neat | 310 | 3.1 | 1.9 | 2.6 | 13 |
| C-10 | COH | NMe$_2$ | p-Diox | 326 | 5.1 | 2.0 | 6.3 | 18 |
| 6 | COCF$_3$ | OPh | p-Diox | 292 | 3.5 | 2.9 | 3.6 | 12 |
| 7 | COCF$_3$ | OMe | p-Diox | 292 | 4.0 | 2.0 | 3.6 | 7.4 |
| 8 | COCF$_3$ | NMe$_2$ | p-Diox | 356 | 5.9 | 2.4 | 10 | 16 |
| 9 | SO$_2$C$_3$F$_7$ | BrPt(PEt$_3$)$_2$ | CHCL$_3$ | — | 2.8 | 6.9 | 7.6 | 29 |
| 10 | SO$_2$C$_3$F$_7$ | BrPd(PPh$_3$)$_2$ | CHCL$_3$ | — | 5.0 | 11 | 1.3 | 53 |

TABLE 2

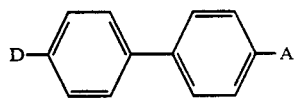

| Compound Number | A | D | solvent | $\lambda_{max}$ (nm) | $\mu$ $10^{-18}$ | $\alpha$ $10^{-23}$ | $\beta$ $10^{-30}$ | $\gamma$ $10^{-36}$ |
|---|---|---|---|---|---|---|---|---|
| C-11 | SO$_2$C$_6$H$_{12}$OH | NMe$_2$ | CHCl$_3$ | 330 | 6.0 | 4.6 | 11 | 38 |
| C-12 | SO$_2$F | NH$_2$ | p-Diox | 330 | 6.5 | 2.9 | 12 | 24 |
| 11 | SO$_2$C$_3$F$_7$ | OMe | p-Diox | 305 | 6.0 | 3.9 | 9.1 | −78 |
| 12 | SO$_2$C$_6$F$_{13}$ | OMe | p-Diox | 305 | 5.9 | 4.6 | 11 | 68 |
| 13 | SO$_2$C$_6$F$_{13}$ | NMe$_2$ | p-Diox | 362 | 8.0 | 5.1 | 25 | 70 |
| C-13 | COCH$_3$ | OMe | p-Diox | 304 | 3.3 | 3.1 | 3.8 | 23 |
| 14 | COCF$_3$ | OMe | p-Diox |  | 4.2 | 3.2 | 7.6 | 35 |

TABLE 3

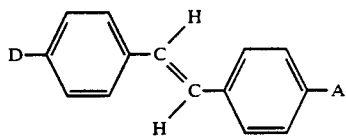

| Compound Number | A | D | solvent | $\lambda_{max}$ (nm) | $\mu$ $10^{-18}$ | $\alpha$ $10^{-23}$ | $\beta$ $10^{-30}$ | $\gamma$ $10^{-36}$ |
|---|---|---|---|---|---|---|---|---|
| C-14 | SO$_2$C$_5$H$_{11}$ | HOHexO | CHCl$_3$ | 336 | 6.5 | 6.0 | 10 | 68 |
| 15 | SO$_2$C$_6$F$_{13}$ | OMe | p-Diox | 347 | 7.8 | 4.8 | 14 | 93 |

TABLE 4

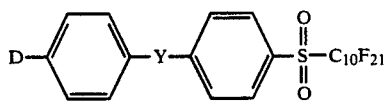

| Compound Number | Y | D | solvent | $\lambda_{max}$ (nm) | $\mu$ $10^{-18}$ | $\alpha$ $10^{-23}$ | $\beta$ $10^{-30}$ | $\gamma$ $10^{-36}$ |
|---|---|---|---|---|---|---|---|---|
| 16 | O | OMe | CHCl$_3$ | 252 | 5.2 | 5.1 | 6.3 | 15 |
| 17 | S | OMe | CHCl$_3$ | 295 | 5.3 | 5.9 | 8.9 |  |

As many differing embodiments of this invention may be made without departing from the spirit and scope thereof, it is to be understood that this invention is not limited to the specific embodiments described except as defined by the appended claims.

We claim:

1. A compound providing for high nonlinearity and high transparency selected from the following structures:

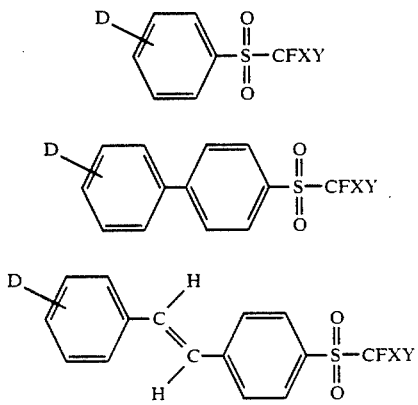

wherein

D is an electron donor moiety selected from $NH_2$, $NHR^1$, $N(C_nH_{2n+1})_2$, $N(C_nH_{2n+1})(C_nH_{2n}OH)$, $N(C_nH_{2n}OH)_2$, $N(C_nH_{2n+1})N(C_nH_{2n+1})_2$, $N=C(C_nH_{2n+1})_2$, $OC_nH_{2n+1}$, $SC_nH_{2n+1}$,

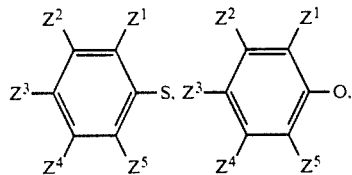

branched or straight chain alkyls having from 2 to 20 carbons, F, and Br, wherein n=0 to 20

$Z^1$, $Z^2$, $Z^3$, $Z^4$ and $Z^5$ are individually selected from H, alkyl of 1 to 20 carbon atoms hydrocarbyl aryl, $OR^2$ and $SR^3$, $R^1$, $R^2$, $R^3$, $R^4$ and $R^5$ are individually selected from hydrocarbyl aryl, alkyl of from 1 to 20 carbon atoms, X and Y are the same or different and are individually selected from H, F, Cl, Br, I, alkyl and fluoroalkyl of 1 to 20 carbon atoms, hydrocarbyl aryl, fluoroaryl, SR and $OR^7$, wherein $R^7$ is selected from alkyl of 1 to 20 carbon atoms and hydrocarbyl aryl, with the proviso for structure 1 that when D is $NH_2$, F, Br, $NH(C_2H_5)$, $N(CH_3)_2$, $OCH_3$, OH or SH, X is not F and Y is not a fluoroalkyl of less than 7 carbon atoms.

2. A compound providing for high nonlinearity and high transparency of the following structure:

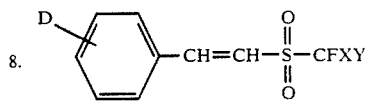

wherein

D is an electron donor moiety selected from $NH_2$, $NHR^1$, $N(C_nH_{2n+1})_2$, $N(C_nH_{2n+1})(C_nH_{2n}OH)$, $N(C_nH_{2n}OH)_2$, $N(C_nH_{2n+1})N(C_nH_{2n+1})_2$, $N=C(C_nH_{2n+1})_2$, $OC_nH_{2n+1}$, $SC_nH_{2n+1}$,

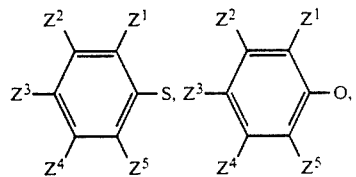

branched or straight chain alkyls having from 2 to 20 carbons, F, and Br, wherein n=0 to 20

$Z^1$, $Z^2$, $Z^3$, $Z^4$ and $Z^5$ are individually selected from H, alkyl of 1 to 20 carbon atoms, hydrocarbyl aryl, $OR^2$ and $SR^3$, $R^1$, $R^2$, $R^3$, $R^4$ and $R^5$ are individually selected from hydrocarbyl aryl, alkyl of from 1 to 20 carbon atoms, X and Y are the same or different and are individually selected from H, F, Cl, Br, I, alkyl and fluoroalkyl of 1 to 20 carbon atoms, hydrocarbyl aryl, fluoroaryl, SR and $OR^7$, wherein $R^7$ is selected from alkyl of 1 to 20 carbon atom sand hydrocarbyl aryl, with the proviso for structure 8 that when D is $OC_nH_{(2n+1)}$, n is not 1.

3. The compound described by claim 1 or 2 wherein X is F and Y is a fluoroalkyl radical having from 1 to 20 carbon atoms.

4. The compound described by claim 1 or 2 wherein X is F and Y is a perfluoroalkyl radical having from 2 to 20 carbon atoms.

* * * * *